United States Patent [19]

Heeres et al.

[11] Patent Number: 5,075,309

[45] Date of Patent: Dec. 24, 1991

[54] ANTIFUNGAL 4-[4-[4-[4-[[2-(2,4-DIFLUOROPHENYL)-2-(1H-AZOLYLMETHYL)-1,3-DIOXOLAN-4-YL]METHOXY]PHENYL]-1-PIPERAZINYL]-PHENYL]TRIAZOLONES AND IMIDAZOLONES

[75] Inventors: Jan Heeres, Vosselaar; Leo J. J. Backx, Arendonk, both of Belgium

[73] Assignee: Janssen Pharmaceutica N. V., Beerse, Belgium

[21] Appl. No.: 517,098

[22] Filed: May 1, 1990

Related U.S. Application Data

[63] Continuation of Ser. No. 363,795, Jun. 9, 1989, abandoned.

[51] Int. Cl.$^5$ .................. A61K 31/495; C07D 405/14
[52] U.S. Cl. ...................... 514/252; 544/366; 544/370
[58] Field of Search ............... 544/366, 370; 514/255, 514/252

[56] References Cited

U.S. PATENT DOCUMENTS

| | | | |
|---|---|---|---|
| 4,267,179 | 5/1981 | Heeres et al. | 544/366 |
| 4,735,942 | 4/1988 | Heeres et al. | 544/366 |
| 4,916,134 | 4/1990 | Heeres et al. | 544/366 |

FOREIGN PATENT DOCUMENTS

| | | | |
|---|---|---|---|
| 0283992 | 9/1988 | European Pat. Off. | 544/366 |
| 539139 | 11/1985 | Spain . | |

OTHER PUBLICATIONS

Chem. Abstract, vol. 106, No. 67318k (1987).
Heeres et al., *J. Med. Chem.*, vol. 27, No. 7, (1984), pp. 894–900.

*Primary Examiner*—Mukund J. Shah
*Assistant Examiner*—Philip I. Datlow
*Attorney, Agent, or Firm*—Charles J. Metz

[57] ABSTRACT

4-[4-[4-[4-[[2-(2,4-difluorophenyl)-2-(1H-azolylmethyl)-1,3-dioxolan-4-yl]methoxy]phenyl]-1-piperazinyl]-phenyl]triazolones and imidazolones, their pharmaceutically acceptable acid addition salts and stereoisomeric forms having improved antifungal properties, compositions containing the same, and methods of inhibiting and/or preventing the growth or the development of fungi, or of destroying fungi, in warm-blooded animals suffering from diseases caused by these fungi.

7 Claims, No Drawings

ANTIFUNGAL 4-[4-[4-[4-[[2-(2,4-DIFLUOROPHENYL)-2-(1H-AZOLYLMETHYL)-1,3-DIOXOLAN-4-YL]METHOXY]PHENYL]-1-PIPERAZINYL]PHENYL]-TRIAZOLONES AND IMIDAZOLONES

CROSS-REFERENCE TO RELATED APPLICATION

This is a continuation-in-part of our copending application Ser. No. 363,795, filed June 9, 1989, now abandoned.

BACKGROUND OF THE INVENTION

In U.S. Pat. Nos. 4,267,179; 4,335,125; 4,735,942, 4,791,111 and 4,916,134 there are described a number of heterocyclic derivatives of (4-phenyl-1-piperazinylaryloxymethyl-1,3-dioxolan-2-yl)methyl-1H-imidazoles and 1H-1,2,4-triazoles, which compounds are taught to possess antifungal and antibacterial properties. In J. Med. Chem. 1984, 27 (7), 894 there is disclosed cis-2-cyclopentyl-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-3H-1,2,4-triazol-3-one as an antifungal compound.

The compounds of the present invention show improved antifungal activity, in particular against Microsporum species and against Candida species.

DESCRIPTION OF THE INVENTION

This invention is concerned with antifungal compounds having the formula

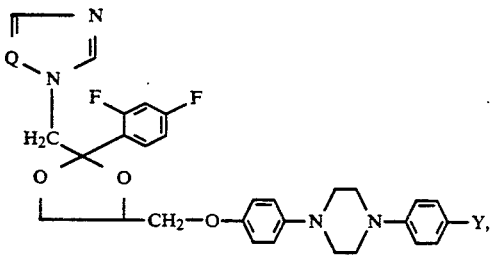

the pharmaceutically acceptable acid addition salts and the stereochemically isomeric forms thereof, wherein
Q is CH or N;
y is a radical of formula

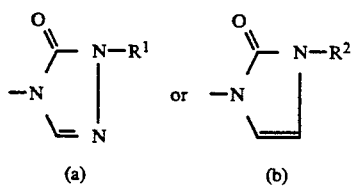

$R^1$ is $C_{5-7}$cycloalkyl or mono-, di-, tri-, tetra- or pentahalo$C_{1-4}$alkyl; and
$R^2$ is $C_{1-6}$alkyl, $C_{5-7}$cycloalkyl or mono-, di-, tri-, tetra- or pentahalo$C_{1-4}$alkyl.

In the foregoing definitions the term "halo" is generic to fluoro, chloro, bromo and iodo; the term "$C_{1-6}$alkyl" defines straight and branched hydrocarbon radicals having from 1 to 6 carbon atoms such as for example, methyl, ethyl, propyl, 1-methylethyl, 1,1-dimethylethyl, 1-methylpropyl, 2-methylpropyl, butyl, pentyl, hexyl and the like; the term "$C_{5-7}$cycloalkyl" defines cyclopentyl, cyclohexyl and cycloheptyl; and the term "mono-, di-, tri-, tetra- or pentahalo$C_{1-4}$alkyl" defines straight and branched hydrocarbon radicals having from 1 to 4 carbon atoms wherein one, two, three, four or five hydrogen atoms are replaced by halo, such as, for example, trifluoromethyl, 2-fluoroethyl, 2,2,2-trifluoroethyl, 2-fluoro-1-methylethyl, 2-fluoro-1-(fluoromethyl)ethyl, 2,2,2-trifluoro-1-methylethyl, 2,2,3,3-tetrafluoropropyl, 2,2,3,3-pentafluoro-1-methylpropyl and the like.

From formula (I) it is evident that the compounds of this invention have at least two asymmetric carbon atoms in their structures, namely those located in the 2- and 4-position of the dioxolane nucleus. Depending on the structure of $R^1$ and $R^2$ further asymmetric centra may be present. Consequently the compounds of formula (I) can exist under different sterochemically isomeric forms. Unless otherwise mentioned or indicated, the chemical designation of compounds denotes the mixture of all possible stereochemically isomeric forms, said mixtures containing all diastereomers and enantiomers of the basic molecular structure. The absolute configuration of each chiral center may be indicated by the sterochemical descriptors R and S, this R and S notation corresponding to the rules described in Pure Appl. Chem. 1976, 45, 11–30. The relative configuration of the asymmetric centers in diastereomeric racemates of formula (I) is denoted by the descriptors cis and trans according to the rules described in J. Org. Chem. 1970, 35 (9), 2849–2867. Stereochemically isomeric forms of the compounds of formula (I) are obviously intended to be embraced within the scope of the invention.

The compounds of formula (I) have basic properties and, consequently, they may be converted to their therapeutically active non-toxic acid addition salt forms by treatment with appropriate acids, such as, for example, inorganic acids, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term pharmaceutically acceptable acid addition salts also comprises the solvates which the compounds of formula (I) may form and said solvates are intended to be included within the scope of the present invention. Examples of such solvates are e.g. the hydrates, alcoholates and the like.

Interesting compounds are those compounds of formula (I) wherein Q is N; and/or the substituents on the dioxolane nucleus have a cis configuration.

Particularly interesting compounds are those interesting compounds wherein $R^1$ and $R^2$ are mono-, di-, tri-, tetra- or pentafluoro$C_{1-4}$alkyl, cyclohexyl or cyclopentyl, or $R^2$ is $C_{1-4}$alkyl.

Preferred compounds are those particularly interesting compounds wherein $R^1$ and $R^2$ are 2,2,2-trifluoroethyl, 2,2,3,3-tetrafluoropropyl, cyclopentyl, or $R^2$ is propyl, 1-methylpropyl, 2-methylpropyl or butyl.

The most preferred compounds are cis-2-cyclopentyl-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-3H-1,2,4-triazol-3-one;

cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(2,2,2-trifluoroethyl)-3H-1,2,4-triazol-3-one; and cis-1-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-1,3-dihydro-3-(1-methylpropyl)-2H-imidazol-2-one, the pharmaceutically acceptable salts thereof and the stereochemically isomeric forms thereof.

In order to simplify the structural representations of the compounds of formula (I) and of certain starting materials and intermediates used in the preparation thereof, the 2-(2,4-difluorophenyl)-2-(1H-1,2,4-azol-1-ylmethyl)-1,3-dioxolan-4-yl group will hereafter be represented by the symbol D:

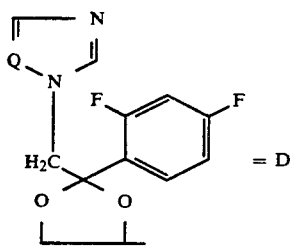

The compounds of formula (I) can be prepared by O-alkylating an appropriately substituted phenol of formula (III) with an alkylating reagent of formula (II).

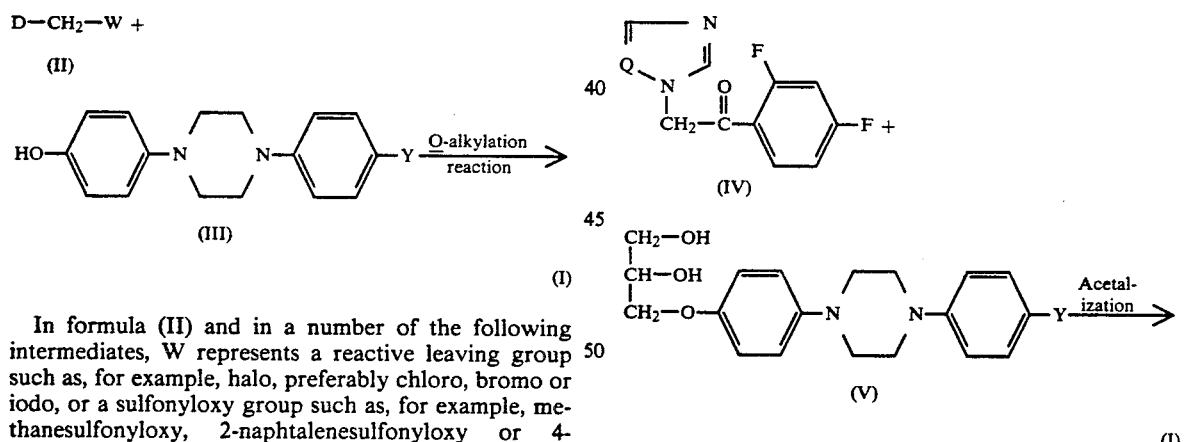

In formula (II) and in a number of the following intermediates, W represents a reactive leaving group such as, for example, halo, preferably chloro, bromo or iodo, or a sulfonyloxy group such as, for example, methanesulfonyloxy, 2-naphtalenesulfonyloxy or 4-methylbenzenesulfonyloxy and the like.

The alkylation reaction of (II) with (III) can be carried out under art-known conditions of performing O-alkylations. Said O-alkylation reaction can conveniently be conducted in a suitable reaction-inert solvent in the presence of an appropriate base. A suitable reaction-inert solvent is, for example, an aromatic hydrocarbon, e.g., benzene, methylbenzene, dimethylbenzene and the like; a halogenated hydrocarbon, e.g., dichloromethane, trichloromethane and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a dipolar aprotic solvent, e.g., N,N-dimethylformamide, N,N-dimethylacetamide, hexamethylphosphoric triamide, dimethyl sulfoxide, nitrobenzene, 1-methyl-2-pyrrolidinone and the like, or a mixture of said solvents. The acid which is liberated during the course of the reaction may be picked up by an appropriate base such as, for example, an alkali or an earth alkaline metal carbonate, hydrogen carbonate, hydroxide, alkoxide, hydride or amide, e.g., sodium carbonate, potassium carbonate, sodium hydroxide, sodium methoxide, sodium hydride, sodium amide and the like, or an organic base such as, for example, an amine, e.g., N,N-diethylethanamine, N-(1-methylethyl)-2-propanamine, 4-ethylmorpholine, and the like. In some instances it may be advantageous to convert the substitued phenol (III) first into a metal salt thereof, preferably the sodium salt, e.g., by the reaction of (III) with a metal base such as sodium hydride, sodium hydroxide and the like, and to use said metal salt subsequently in the reaction with (II). Stirring and somewhat elevated temperatures may enhance the rate of the reaction; more particularly the reaction may be conducted at a temperature from about 50° C. to about 60° C. Additionally, it can be advantageous to conduct said O-alkylation under an inert atmosphere such as, for example, oxygen-free nitrogen or argon gas.

Alternatively, the compounds of formula (I) may be prepared following the procedures described in U.S. Pat. No. 4,101,666, which is incorporated herein by reference, for instance, by the acetalation reaction of a ketone of formula (IV) with a 2,3-dihydroxypropyl ether derivative of formula (V) in the presence of an acid such as, for example, benzenesulfonic acid, 4-methylbenzenesulfonic acid, methanesulfonic acid and the like acids.

Said acetalization reaction can conveniently be conducted in a reaction-inert solvent such as, an aromatic hydrocarbon, e.g., benzene, methylbenzene, a halogenated hydrocarbon, e.g., trichloromethane; an alkanol, e.g., ethanol, propanol, butanol and the like, or a mixture of such solvents. Preferably, the water which is liberated during the course of the reaction, is removed by azeotropical distillation. In a similar way, the compounds of formula (I) may also be obtained by transacetalation of (IV) with the acetone acetal of (V), or by acetalation of (IV) with the 2,3-epoxypropyl ether derivative corresponding to (V), in the presence of an acid and a reaction-inert solvent as described hereinbefore.

Or, the compounds of formula (I) may also be synthesized by N-alkylating an azole (VI) with an intermediate of formula (VII).

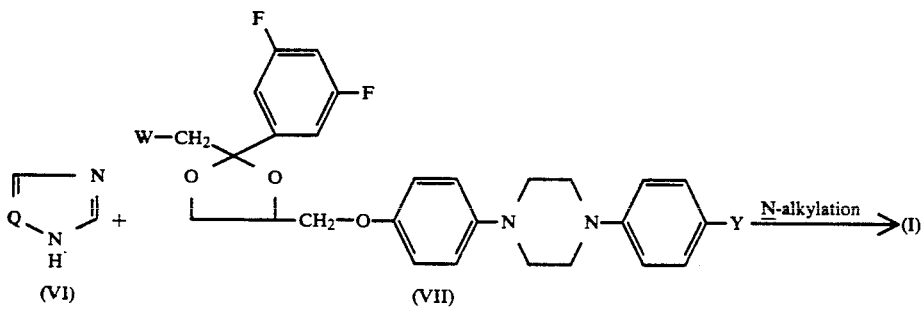

Said N-alkylation reaction can conveniently be conducted in a suitable reaction-inert solvent or a mixture of such solvents in the presence of an appropriate base. Suitable reaction-inert solvents are, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a dipolar aprotic solvent, e.g., N,N-dimethylformamide, N,N-dimethylacetamide, dimethyl sulfoxide, nitrobenzene, 1-methyl-2-pyrrolidinone, and the like; a halogenated hydrocarbon, e.g., dichloromethane, trichloromethane and the like. The addition of an appropriate base such as, for example, an alkali or an earth alkaline metal carbonate, hydrogen carbonate, hydroxide, amide or hydride, e.g., sodium hydroxide, potassium hydroxide, potassium carbonate, sodium hydride and the like or an organic base such as, for example, N,N-dimethyl-4-pyridinamine, N,N-diethylethanamine or N-(1-methylethyl)-2-propanamine may be employed to pick up the acid which is liberated during the course of the reaction. In some instances it may be advantageous to use an excess of the azole (VI) or to convert it to its metal salt form, in particular its alkali metal salt form following art-known procedures such as, e.g. by treatment of the azole (VI) with an alkali metal hydroxide, alkoxide, amide or hydride.

The compounds of formula (I) may also be obtained by cyclizing an intermediate of formula (VIII) with an appropriately substituted benzenamine of formula (IX), or by cyclizing a benzenamine of formula (X) with a reagent of formula (XI).

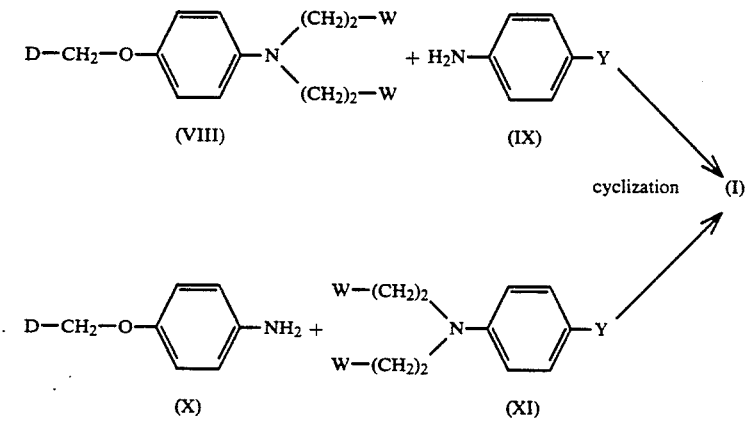

Said cyclization reaction may be carried out by stirring the reactants in the presence of an appropriate polar solvent, e.g. water, in admixture with an appropriate water-miscible organic solvent, such as, for example, 2-propanol, 2-propanone and the like, preferably at an elevated temperature and most preferably, in the presence of an alkali or earth alkaline metal iodide such as, e.g., potassium iodide.

Furthermore, the compounds of formula (I) may be prepared by N-alkylating a piperazine of formula (XII) with a benzene of formula (XIII), or by N-alkylating a piperazine of formula (XV) with a benzene of formula (XIV) following standard N-alkylating procedures. In formulae (XIII) and (XIV) $W^1$ represents an appropriate reactive leaving group, such as, for example, halo, e.g., chloro or bromo and in particular fluoro, or a sulfonyloxy group, e.g. trifluoromethanesulfonyloxy.

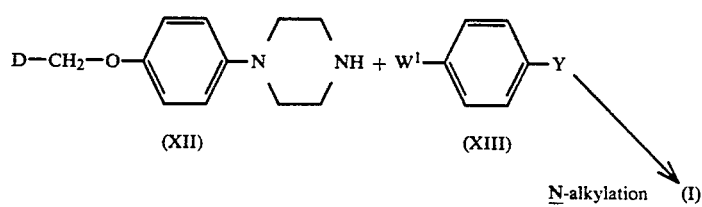

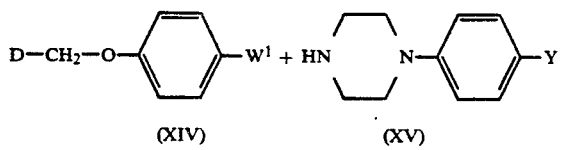

Said N-alkylation may be carried out by stirring the reactants, preferably at somewhat elevated temperatures, in an appropriate organic solvent such as, for example, N,N-dimethylformamide, N,N-dimethylacetamide, dimethyl sulfoxide and the like, in the presence of an appropriate base such as, for example, an alkali metal hydride or carbonate and the like bases.

The compounds of formula (I) wherein Y is a radical of formula (a), said compounds being represented by formula (I-a), can generally be prepared by cyclizing an intermediate of formula (XVI) with an appropriate reagent of formula (XVII) and the compounds wherein Y is a radical of formula (b), said compounds being represented by formula (I-b), can generally be prepared by cyclizing and intermediate of formula (XVI) with an appropriate reagent of formula (XVIII).

previously defined meaning. Said cyclization reaction can generally be conducted in a suitable reaction-inert solvent such as, for example, an alcohol, e.g., butanol and the like; an ether, e.g., tetrahydrofuran, 1,4-dioxane, 1,1'-oxybis(2-methoxyethane); tetrahydrothiophene 1,1-dioxide and the like solvents. Although the cyclization reaction may be conducted at room temperature, somewhat elevated temperatures are appropriate to enhance the rate of the reaction. Preferably the reaction is conducted at the reflux temperature of the reaction mixture.

The compounds of formula (I-a) may alternatively be prepared by cyclizing an intermediate of formula (XIX) with an amidine of formula (XX) or an acid addition salt thereof, and N-alkylating the thus obtained intermediate with a reagent of formula (XXI).

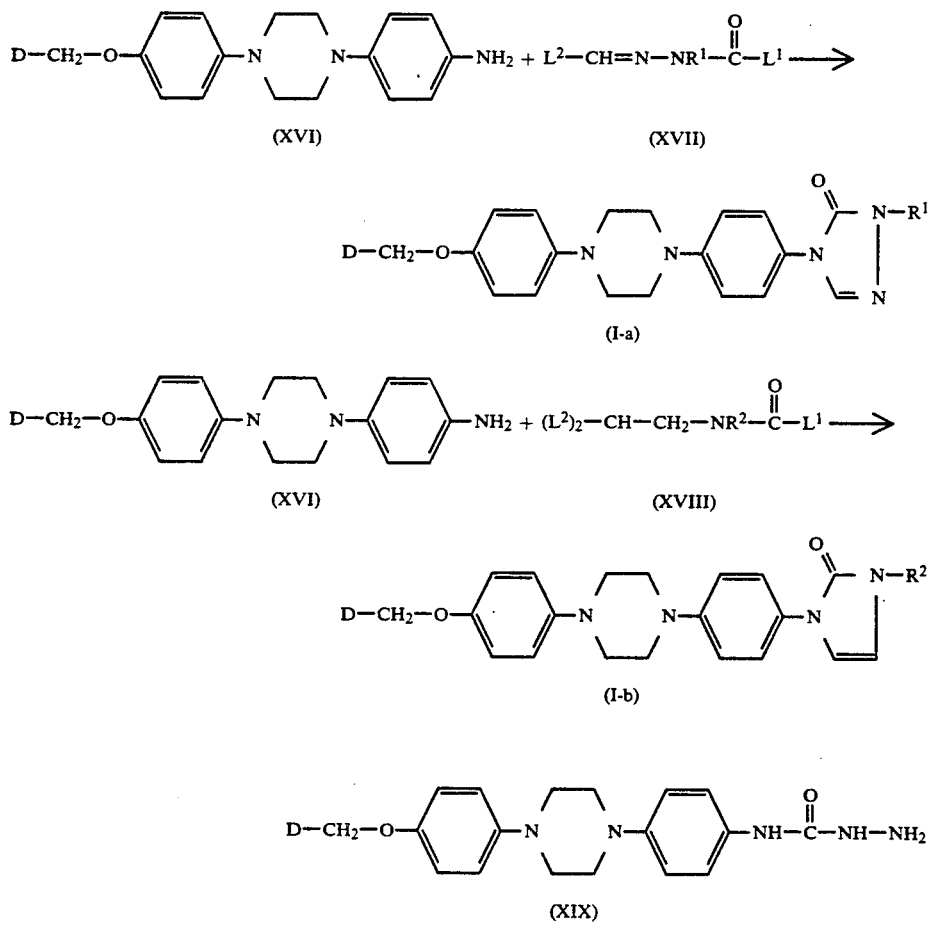

In formulae (XVII) and (XVIII) and hereinafter $L^1$ and $L^2$ both represent an appropriate leaving group such as, for example, $C_{1-6}$alkyloxy, aryloxy, di($C_{1-4}$alkyl)-amino and the like groups and $R^1$ and $R^2$ have the Said cyclization may be carried out by mixing and heating the reactants, preferably, in the presence of an appropriate reaction-inert organic solvent having a relatively high boiling point such as, for example, 1,1'-oxybis(2-methoxyethane).

Said N-alkylation reaction may easily be performed following the same procedure as outlined for the preparation of compounds of formula (I) from (VI) and (VII). It may be advantageous however, to convert the intermediate first into a metal salt form thereof, preferably the sodium salt, in the usual manner, e.g., by reaction with a metal base such as sodium hydride, sodium hydroxide and the like bases, and to use said metal salt subsequently in the reaction with (XXI). The addition of a iodide salt, preferably an alkali iodide, may be appropriate. Somewhat elevated temperatures and stirring may enhance the rate of the reaction.

The compounds of formula (I-b) can alternatively be prepared by cyclizing an intermediate of formula (XXII) with a reagent of formula (XXIII).

ates of formula (V) can be obtained by O-alkylating an intermediate of formula (III) with (chloromethyl)oxirane and subsequent hydrolysis of the epoxide.

The previously described intermediates and starting materials may also be converted into each other following art-known functional group transformation procedures.

The compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by

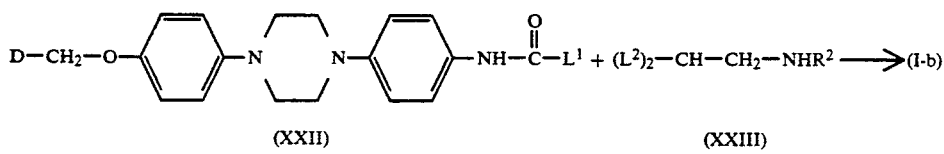

(XXII)  (XXIII)

Said cyclization reaction can be carried out by stirring and heating the reactants in a reaction-inert solvent such as, for example, an ether, e.g. tetrahydrofuran, 1,4-dioxane and the like, in the presence of an appropriate acid such as, for example, formic, acetic, propanoic, benzoic and the like acids.

A number of intermediates and starting materials used in the foregoing preparations are known compounds, others may be prepared according to art-known methodologies of preparing said or similar compounds, while still others are new. A number of such preparation methods will be described hereinafter in more detail.

The intermediates of formula (III), (XVI) and (XIX) can conveniently be prepared following procedures analogous to those described in U.S. Pat. Nos. 4,267,179; 4,335,125; 4,735,942 and 4,791,111, which are incorporated herein by reference, and those described in EP-0,331,232.

Starting materials of formula (II) may be derived from a 1-(2,4-difluorophenyl)-2-haloethanone by reacting the latter with an azole (VI) in an reaction inert solvent, if appropriate in the presence of a base, and subsequently reacting the thus obtained 1-(2,4-difluorophenyl)-2-(azol-1-yl)ethanone (IV) with 1,2,3-propanetriol in a suitable acetalizing medium. It may be particularly desirable to separate cis and trans forms at this early stage. Appropriate methods which may be employed include, for example, selective crystallization, chromatographical separations such as column chromatography and the like methods. The desired alkylating reagents of formula (II) can easily by prepared by converting the remaining hydroxy group of the obtained intermediate into a reactive leaving group according to methodologies generally known in the art. Said reactive derivatives of formula (II) can alternatively be prepared according to a sequence of reactions similar to the procedures described in U.S. Pat. No. 4,267,179. The intermediates of formula (VII) are prepared following procedures described in U.S. Pat. No. 4,101,666, which is incorporated herein by reference, e.g., by the acetalization reaction of a diol of formula (V) with a 1-(2,4-difluorophenyl)-2-haloethanone. In turn, the intermedifirst converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Enantiomers may also be separated by chromatography of the racemate over a chiral stationary phase.

Pure stereochemically isomeric forms of the compounds of formula (I) may also be obtained from the pure stereochemically forms of the appropriate intermediates and starting materials, provided that the intervening reactions occur stereospecifically. The pure and mixed stereochemically isomeric forms of the compounds of formula (I) are intended to be embraced within the scope of the present invention.

The compounds of formula (I), the pharmaceutically acceptable acid addition salts and stereochemically isomeric forms thereof show antifungal activity. The latter activity of the compounds of formula (I) can be demonstrated in the "Topical and oral treatment of vaginal candidosis in rats" test; "Topical and oral treatment of microsporosis in guinea pigs" test; "Topical and oral treatment of skin candidosis in guinea pigs" and "Oral treatment of deep (systemic) candidosis in guinea pigs".

In view of their useful antifungal activity, the subject compounds may be formulated into various pharmaceutical forms for administration purposes.

To prepare the pharmaceutical compositions of this invention, an antifungally effective amount of the particular compound, optionally in acid addition salt form, as the active ingredient is combined in intimate admixture with a pharmaceutically acceptable carrier, which carrier may take a wide variety of forms depending on the desired mode of administration. These pharmaceutical compositions are preferably in unitary dosage form suitable for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of formula (I), the pharmaceutically acceptable acid addition salts and stereochemically isomeric forms thereof are useful agents in combatting fungi. For example, said compounds are found to be highly active against a wide variety of fungi such as, for example, *Microsporum canis, Pityrosporum ovale, Ctenomyces mentagrophytes, Trichophyton rubrum, Phialophora verrucosa, Cryptococcus neoformans, Candida tropicalis, Candida albicans,* Mucor species, *Aspergillus fumigatus, Sporotrichum schenckii* and Saprolegnia species. In view of their potent, topical as well as systemic, antifungal activity the compounds of this invention constitute useful tools for the destruction of fungi, or for the inhibition or prevention of the growth or development of fungi. More particularly they can effectively be used in the treatment of warm-blooded animals suffering from diseases such as, for example, tinea corporis, tinea cruris, tinea manus, tinea pedis, candidosis, pityriasis versicolor, onychomycosis, perionyxis, paracoccidioidomycosis, histoplasmosis, coccidiodomycosis, cryptococcosis, chromomycosis, mucormycosis, sporotrichosis, seborrheic dermatitis and the like.

A number of compounds of the present invention are particularly attractive due to their improved topical action against Microsporum species and are therefore particularly useful in the treatment of warm-blooded animals suffering from microsporosis, i.e. infection by Microsporum. Particular examples of said warm-blooded animals are domestic animals such as, for example, dogs, cats and horses, and humans infected by Microsporum.

Further the compounds of the present invention also show an improved activity against Candida infections. The present compounds therefor appear to be particularly useful in the topical treatment of vaginal candidosis and skin candidosis, and in the systemic treatment of skin candidosis and especially deep (or systemic) candidosis.

Those of skill in treating warm-blooded animals suffering from diseases caused by fungi could easily determine the effective amount from the test results presented here. In general it is contemplated that an effective amount would be from 0.01 mg/kg to 50 mg/kg body weight, and more preferably from 0.05 mg/kg to 20 mg/kg body weight. For topical applications it is contemplated that an effective amount would be from 0.001% to 5% (by weight) and more preferably from 0.1% to 2% (by weight).

The following examples are intended to illustrate and not to limit the scope of the present invention. Unless otherwise stated all parts therein are by weight.

EXPERIMENTAL PART

A. Preparation of the Intermediates

EXAMPLE 1 a) To a refluxing and stirred solution of 457.6 parts of 1H-imidazole in 2400 parts of trichloromethane was added dropwise a solution of 320 parts of 2-chloro-1-(2,4-difluorophenyl)ethanone in 1440 parts of trichloromethane. After stirring for ½ hour at reflux temperature, the reaction mixture was poured into water. The organic layer was washed with water (2x), dried, filtered and evaporated. The residue was crystallized from 2-propanol, yielding 244 parts (69%) of 1-(2,4-difluorophenyl)-2-(1H-imidazol-1-yl)ethanone; mp. 125° C. (interm. 1).

b) A mixture of 100 parts of 1,2,3-propanetriol, 70 parts of intermediate (1), 450 parts of methanesulfonic acid and 108 parts of benzene was stirred for 2 hours at reflux temperature using a water separator. After cooling, the reaction mixture was added dropwise to a stirred sodium hydrogen carbonate solution. The product was extracted with trichloromethane and the extract was washed with water, dried, filtered and evaporated, yielding 80 parts (100%) of (cis+trans)-2-(2,4-difluorophenyl)-2-(1H-imidazol-1-ylmethyl)-1,3-dioxolane-4-methanol (interm. 2).

c) To a stirred mixture of 266.5 parts of intermediate (2), 234 parts of N,N-diethylethanamine, 8 parts of N,N-dimethyl-4-pyridinamine and 1950 parts of dichloromethane were added portionwise 227 parts of 2-naphthalenesulfonyl chloride. Stirring was continued overnight at room temperature. The reaction mixture was diluted with water and extracted with dichloromethane (3x). The combined extracts were washed with water, dried, filtered and evaporated. The residue was purified twice by column chromatography (silica gel; CHCl₃/CH₃OH 99:1; HPLC; silica gel; CH₂Cl₂/CH₃OH 99:1). The eluent of the desired fraction was evaporated and the residue was crystallized from 4-methyl-2-pentanone. The product was filtered off and dried, yielding 100 parts (22.8%) of cis-[[2-(2,4-difluorophenyl)-2-(1H-imidazol-1-ylmethyl)-1,3-dioxolan-4-yl]methyl] 2-naphthalenesulfonate; mp. 125.0° C. (interm. 3).

EXAMPLE 2

A mixture of 44.6 parts of 1-(2,4-difluorophenyl)-2-(1H-1,2,4-triazol-1-yl)ethanone (described in GB-2,099,818), 56.0 parts of (2S)-1,2,3-propanetriol 1-(4-methylbenzenesulfonate) (ester), 296 parts of methanesulfonic acid and 200 parts of dichloromethane was stirred at reflux temperature using a water separator. After cooling, the reaction mixture was added dropwise to a mixture of ice-water, diluted potassium carbonate and dichloromethane. The organic layer was separated and the aqueous phase was re-extracted with dichloromethane. The combined dichloromethane layers were dried, filtered and evaporated. The residue was purified by column chromatography (silica gel; CHCl₃). The eluent of the desired fraction was evaporated and the residue was converted into the 4-methylbenzenesulfonate salt in 4-methyl-2-pentanone. The salt was recrystallized from 4-methyl-2-pentanone, yielding 20.5 parts (16.4%) of (−)-(2S,cis)-2-(2,4-difluorophenyl)-2-(1H-1,2,4-triazol-1-ylmethyl)-1,3-dioxolane-4-methanol 4-methylbenzenesulfonate(ester) 4-methylbenzenesulfonate (salt) (1:1); mp. 182.5° C.; $[\alpha]_D^{20} = -13.79°$ (c=1% in CH₃OH) (interm. 4).

EXAMPLE 3

A mixture of 40.0 parts of 1-(2,4-difluorophenyl)-2-(1H-1,2,4-triazol-1-yl)ethanone (described in GB-2,099,818), 56.0 parts of (2R)-1,2,3-propanetriol 1-(4-methylbenzenesulfonate) (ester), 370 parts of methanesulfonic acid and 133 parts of dichloromethane was stirred for 24 hours at reflux temperature using a water separator. After cooling, the reaction mixture was added dropwise to a mixture of potassium carbonate, ice-water and dichloromethane. The organic layer was separated, washed with water, dried, filtered and evaporated. The residue was purified by column chromatography (silica gel; CHCl₃). The eluent of the desired fraction was evaporated and the residue was converted into the 4-methylbenzenesulfonate salt in 4-methyl-2-pentanone. The salt was recrystallized from acetonitrile, yielding 23.1 parts (20.6%) of (+)-(2R,cis)-2-(2,4-difluorophenyl)-2-(1H-1,2,4-triazol-1-ylmethyl)-1,3-dioxolane-4-methanol 4-methylbenzenesulfonate(ester) 4-methylbenzenesulfonate (salt,1:1); mp. 183.5° C.; $[\alpha]_D^{20} = +14.43°$ (c=1% in CH₃OH) (interm. 5).

EXAMPLE 4 a) 40 Parts of 2,2-(dimethoxy)ethanamine were reductively alkylated with 35 parts of 3-pentanone in a mixture of 4 parts of palladium-on-charcoal catalyst (10%), 2 parts of a solution of thiophene in methanol (4%) and 395 parts of methanol. The reaction mixture was filtered and the filtrate was evaporated. The residue was distilled (waterjet pump; 76° C.), yielding 55.7 parts (83.6%) of N-(2,2-dimethoxyethyl)-1-ethylpropanamine (interm. 6).

b) A mixture of 36 parts of phenyl [4-[4-(4-methoxyphenyl)-1-piperazinyl]phenyl]carbamate monohydrochloride (described in example XVII of U.S. Pat. No. 4,267,179), 19.2 parts of intermediate (6), 4 parts of N,N-dimethyl-4-pyridinamine, 14.6 parts of N,N-diethylethanamine and 412 parts of 1,4-dioxane was stirred for 3 hours at reflux temperature. After cooling, the reaction mixture was diluted with water and the whole was left to crystallize. The product was filtered off, washed with water, dried and stirred in 122 parts of formic acid for 3 hours at 70° C. The whole was evaporated and the residue was boiled in 2-propanol and further purified by column chromatography (silica gel; CH₂Cl₂/CH₃OH 99:1). The eluent of the desired fraction was evaporated and the residue was triturated in 2-propanol. The product was filtered off and dried, yielding 29.3 parts (85.0%) of 1-(1-ethylpropyl)-1,3-dihydro-3-[4-[4-(4-methoxyphenyl)-1-piperazinyl]phenyl]-2H-imidazol-2-one; mp. 195.8° C. (interm. 7).

EXAMPLE 5 a) A mixture of 10 parts of phenyl [4-[4-(4-methoxyphenyl)-1-piperazinyl]phenyl]carbamate monohydrochloride (described in example XVII of U.S. Pat. No. 4,267,179), 3 parts of 2,2-diethoxy-ethanamine and 100 parts of 1,4-dioxane was stirred for 6 hours at reflux temperature. After cooling, the precipitate was filtered off, washed with 1,4-dioxane and purified by column chromatography (silica gel; CHCl₃/CH₃OH 99:1). The eluent of the desired fraction was evaporated and the residue was crystallized from 1,4-dioxane, yielding 3.9 parts of N-(2,2-dimethoxyethyl)-N'-[4-[4-(4-methoxyphenyl)-1-piperazinyl]phenyl]urea; mp. 225° C. (interm. 8).

b) A mixture of 70 parts of intermediate (8), 84 parts of hydrochloric acid, 300 parts of water and 280 parts of methanol was stirred for ½ hour at 80° C. After cooling, the reaction mixture was left to crystallize. The product was filtered off, washed with water and dried, yielding 24.5 parts (37%) of 1,3-dihydro-1-[4-[4-(4-methoxyphenyl)-1-piperazinyl]phenyl]-2H-imidazol-2-one monohydrochloride monohydrate; mp. 256.2° C. (interm. 9).

c) To a stirred mixture of 12 parts of intermediate (9), 6.75 parts of 1-bromopropane and 250 parts of dimethyl sulfoxide were added 3 parts of a dispersion of sodium hydride in mineral oil (50%). After stirring for 2 hours at 60° C. and subsequent cooling, the reaction mixture was poured into water. The precipitate was filtered off and purified by column chromatography (silica gel; CHCl₃). The eluent of the desired fraction was evaporated and the residue was crystallized from 1-butanol. The product was filtered off and dried, yielding 7.2 parts (61%) of 1,3-dihydro-1-[4-[4-(4-methoxyphenyl)-1-piperazinyl]-phenyl]-3-propyl-2H-imidazol-2-one; mp. 214.1° C. (interm. 10). In a similar manner intermediate (9) was converted into 1,3-dihydro-1-[4-[4-(4-methoxyphenyl)-1-piperazinyl]phenyl]-3-(1-methylpropyl)-2H-imidazol-2-one; mp. 184.0° C. (interm. 11).

EXAMPLE 6 a) To a stirred solution of 25.0 parts of 2,2,2-trifluoroethanol in 175 parts of N,N-diethylethanamine were added portionwise 62.2 parts of 2-naphthalenesulfonyl chloride and then a mixture of 1.5 parts of N,N-dimethyl-4-pyridinamine and 25 parts of ethyl acetate. After stirring overnight at room temperature, the reaction mixture was filtered and the filtrate was evaporated. The residue was stirred in water. The solid was filtered off and dissolved in dichloromethane. This solution was dried, filtered and evaporated. The residue was successively triturated with petroleumether and crystallized from 2-propanol. The product was filtered off and dried, yielding 65.3 parts (89%) of 2,2,2-trifluoroethyl 2-naphthalenesulfonate; mp. 72.7° C. (interm. 12).

b) A mixture of 17.5 parts of intermediate (9), 16.1 parts of intermediate (12), 10.6 parts of sodium carbonate, 261 parts of 1,3-dimethyl-2-imidazolidinone and 130.5 parts of methylbenzene was stirred for 48 hours at reflux temperature using a water separator. After cooling, the reaction mixture was diluted with water. Upon addition of some petroleumether and 4.2 parts of acetic acid, the product crystallized out. It was dried and purified by column chromatography (silica gel; CH$_2$Cl$_2$/CH$_3$OH 99.5:0.5). The eluent of the desired fraction was evaporated and the residue was crystallized from 4-methyl-2-pentanone. The product was filtered off and dried, yielding 9.0 parts (41.6%) of 1,3-dihydro-1-[4-[4-(4-methoxyphenyl)-1-piperazinyl]-phenyl]-3-(2,2,2-trifluoroethyl)-2H-imidazol-2-one; mp. 224.1° C. (interm. 13).

EXAMPLE 7

To a stirred and cooled (ice-bath) amount of 200 ml of a boron tribromide solution in dichloromethane 1M was added dropwise a solution of 14.6 parts of 1,3-dihydro-1-[4-[4-(4-methoxyphenyl)-1-piperazinyl]phenyl]-3-methyl-2H-imidazol-2-one in 665 parts of dichloromethane. Stirring was continued for 5 days at room temperature and then the reaction mixture was poured into a mixture of 200 parts of water, 158 parts of methanol and 180 parts of ammonium hydroxide. After stirring for 1 hour, the precipitate was filtered off, washed with dichloromethane and water and dried (=first fraction of product). The organic layer of the filtrate was separated and evaporated. The residue was triturated in dichloromethane. The solid was filtered off and dried (=second fraction). The two fractions were combined and crystallized from N,N-dimethylformamide, yielding 9.6 parts (68.5%) of 1,3-dihydro-1-[4-[4-(4-hydroxyphenyl)-1-piperazinyl]phenyl]-3-methyl-2H-imidazol-2-one; mp. 283.1° C. (interm. 14).

Following the same procedure there were also prepared the intermediates of Table 1.

TABLE 1

HO—⟨phenyl⟩—N⟨piperazine⟩N—⟨phenyl⟩—N⟨imidazolone with C=O, N—R$^2$⟩

| Interm. No. | R$^2$ | Physical data (mp.) |
|---|---|---|
| 14 | CH$_3$ | 283.1° C. |
| 15 | C$_2$H$_5$ | 241.2° C. |
| 16 | n.C$_3$H$_7$ | 246.1° C. |
| 17 | i.C$_3$H$_7$ | 249.5° C. |
| 18 | n.C$_4$H$_9$ | 195.0° C. |
| 19 | CH(CH$_3$)C$_2$H$_5$ | 219.6° C. |
| 20 | CH$_2$CH(CH$_3$)$_2$ | 224.5° C. |
| 21 | CH(CH$_3$)C$_3$H$_7$ | 184.9° C. |
| 22 | CH(C$_2$H$_5$)$_2$ | 219.5° C. |
| 23 | CH(CH$_3$)CH(CH$_3$)$_2$ | 238.2° C. |
| 24 | c.C$_5$H$_9$ | 230.8° C. |
| 25 | c.C$_6$H$_{11}$ | 261.8° C. |
| 26 | CH$_2$CF$_3$ | 227.7° C. |

EXAMPLE 8

A mixture of 52.8 parts of 2,2,3,3-tetrafluoro-1-propanol, 117.8 parts of 2-naphthalenesulfonyl chloride, 294 parts of pyridine and 2.0 parts of N,N-dimethyl-4-pyridinamine was stirred for 48 hours at room temperature. The reaction mixture was diluted with water and the whole was left to crystallize. The product was filtered off, washed with water and recrystallized from 2-propanol, yielding 98.2 parts (76.2%) of 2,2,3,3-tetrafluoropropyl 2-naphthalenesulfonate; mp. 89.6° C. (interm. 27).

EXAMPLE 9 a) To a cooled (ice-bath) suspension of 41.7 parts of 2-naphthalenesulfonyl chloride in 174 parts of methylbenzene were added dropwise 20.0 parts of 1,1,1-trifluoro-2-propanol. After stirring for 1 hour, there was added dropwise a mixture of 9.6 parts of a dispersion of sodium hydride in mineral oil (50%) and some methylbenzene while cooling on ice. Subsequently, the whole was diluted dropwise with water. The organic layer was separated, dried, filtered and evaporated, yielding 53.2 parts (99.9%) of (2,2,2-trifluoro-1-methylethyl) 2-naphthalenesulfonate (interm. 28).

b) A mixture of 17.5 parts of 2,4-dihydro-4-[4-(4-methoxyphenyl)-1-piperazinyl]phenyl]-3H-1,2,4-triazol-3-one (described in Example XVII of U.S. Pat. No. 4,267,179), 22.0 parts of intermediate (28), 5.0 parts of lithium carbonate, 10.0 parts of sodium carbonate, 261 parts of 1,3-dimethyl-2-imidazolidinone and 130.5 parts of methylbenzene was stirred for 4 days at reflux temperature. After cooling, the reaction mixture was diluted with 1500 parts of water. Upon addition of 218 parts of 2,2'-oxybispropane, the product crystallized out. The mother liquor was filtered off and the product was dissolved in dichloromethane. The latter solution was filtered and the filtrate was evaporated, yielding a first fraction of product. The mother liquor was extracted with a mixture of 2,2'-oxybispropane and methylbenzene (1:1). The extract was dried, filtered and evaporated, yielding a second fraction of product. The combined fractions were purified by column chromatography (silica gel; CHCl$_3$). The eluent of the desired fraction was evaporated and the residue was crystallized from 4-methyl-2-pentanone, yielding 6 parts (26.8%) of 2,4-dihydro-4-[4-[4-(4-methoxyphenyl)-1-piperazinyl]phenyl]-2-(2,2,2-trifluoro-1-methylethyl)-3H-1,2,4-triazol-3-one; mp. 198.7° C. (interm. 29).

c) A mixture of 11.5 parts of intermediate (29), 522 parts of hydrobromic acid 48% and 3.0 parts of sodium sulfite was stirred overnight at reflux temperature. After cooling, the reaction mixture was diluted with 1000 parts of water and subsequently neutralized with ammonia. The precipitate was filtered off, dried and purified by column chromatography (silica gel; CHCl$_3$/CH$_3$COOC$_2$H$_5$/hexane/CH$_3$OH 498.5:300:200:1.5). The eluent of the desired fraction was evaporated and the residue was crystallized from 1-butanol. The product was filtered off and dried, yielding 8.4 parts (74.5%) of 2,4-dihydro-4-[4-[4-(4-hydroxyphenyl)-1-piperazinyl]phenyl]-2-(2,2,2-trifluoro-1-methylethyl)-3H-1,2,4-triazol-3-one; mp. 230.4° C. (interm. 30).

In a similar manner intermediate (27) was converted into 2,4-dihydro-4-[4-[4-(4-hydroxyphenyl)-1-piperazinyl]phenyl]-2-(2,2,3,3-tetrafluoropropyl)-3H-1,2,4-triazol-3-one; mp. 214.7° C. (interm. 31).

B. Preparation of the final compounds

EXAMPLE 10

A mixture of 4.2 parts of 2,4-dihydro-4-[4-[4-(4-hydroxyphenyl)-1-piperazinyl]phenyl]-2-(2,2,2-trifluoroethyl)-3H-1,2,4-triazol-3-one (prepared as described in example 15 of EP-0,331,232), 6.4 parts of cis-[[2-(2,4-difluorophenyl)-2-(1H-1,2,4-triazol-1-ylmethyl)-1,3-dioxolan-4-yl]methyl]-2-naphthalenesulfonate (prepared as described in example 2 of U.S. Pat. No. 4,791,111), 1.0 part of sodium hydroxide and 135 parts of N,N-dimethylformamide was stirred at 50° C. under a nitrogen atmosphere. After the addition of water and 1.6 parts of acetic acid, the precipitate was filtered off and taken up in trichloromethane. The organic layer was dried, filtered and evaporated. The residue was purified by column chromatography (silica gel; $CHCl_3/CH_3OH$ 98.5:1.5). The eluent of the desired fraction was evaporated and the residue was crystallized from 4-methyl-2-pentanone, yielding 4.3 parts (62%) of cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(2,2,2-trifluoroethyl)-3H-1,2,4-triazol-3-one; mp. 177.6° C. (compound 2).

In a similar manner using an equivalent amount of 2-cyclopentyl-2,4-dihydro-4-[4-[4-(4-hydroxyphenyl)-1-piperazinyl]phenyl]-3H-1,2,4-triazol-3-one (prepared as described in example 14 of EP-0,331,232) there was also prepared cis-2-cyclopentyl-4-[4-[4-[4-[[2-(2,4-difluorophenyl)-2-(1H-1,2,4-triazol-1-ylmethyl)-1,3-dioxolan-4-yl]methoxy]-phenyl]-1-piperazinyl]phenyl]-2,4-dihydro-3H-1,2,4-triazol-3-one; 218.8° C. (compound 1).

EXAMPLE 11

A mixture of 5 parts of phenyl cis-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-carbamate (prepared as described in example 3 of U.S. Pat. No. 4,791,111), 1.8 parts of N-(2,2-dimethoxyethyl)-2-butanamine, 1 part of N,N-dimethyl-4-pyridinamine and 100 parts of 1,4-dioxane was stirred overnight at reflux temperature. The reaction mixture was evaporated and the residue was stirred for 2 hours in 120 parts of formic acid at 60° C. After evaporation, the residue was dissolved in dichloromethane and the whole was neutralized with a sodium hydrogen carbonate solution. The organic layer was separated, dried, filtered and evaporated. The residue was purified by column chromatography (silica gel; $CHCl_3/CH_3OH$ 99:1). The eluent of the desired fraction was evaporated and the residue was crystallized twice from 4-methyl-2-pentanone, yielding 2.8 parts (55.5%) of cis-1-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-1,3-dihydro-3-(1-methylpropyl)-2H-imidazol-2-one; mp. 159.0° C. (compound 3).

All other compounds in Table 2 were prepared following the procedure described in Example 10.

TABLE 2

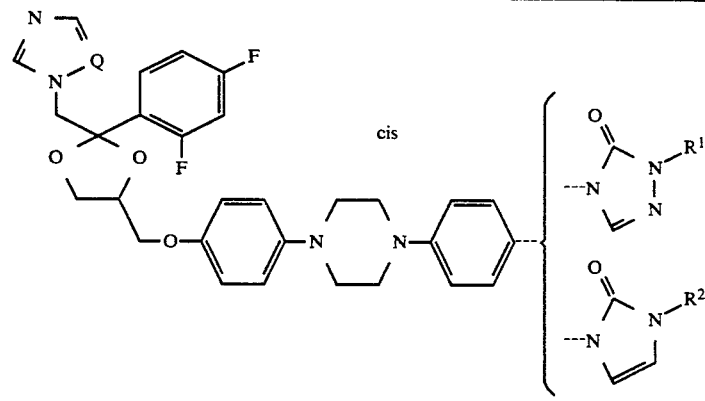

| Comp. No. | Q  | $R^1$ or $R^2$ | Physical data |
|-----------|----|----|----|
| 1  | N  | $R^1 = c.C_5H_9$       | 218.8° C. |
| 2  | N  | $R^1 = CH_2CF_3$       | 177.6° C. |
| 3  | N  | $R^2 = CH(CH_3)C_2H_5$ | 159.0° C. |
| 4  | CH | $R^2 = CH(CH_3)C_2H_5$ | 169.1° C. |
| 5  | N  | $R^2 = CH_3$           | 229.2° C. |
| 6  | CH | $R^2 = CH_3$           | 251.1° C. |
| 7  | N  | $R^2 = CH_2CF_3$       | 197.6° C. |
| 8  | N  | $R^2 = C_2H_5$         | 222.1° C. |
| 9  | CH | $R^2 = C_2H_5$         | 243.4° C. |
| 10 | N  | $R^2 = CH(CH_3)_2$     | 204.5° C. |
| 11 | CH | $R^2 = CH(CH_3)_2$     | 200.5° C. |
| 12 | N  | $R^2 = C_3H_7$         | 188.9° C. |
| 13 | CH | $R^2 = C_3H_7$         | 202.3° C. |
| 14 | N  | $R^2 = C_4H_9$         | 165.9° C. |
| 15 | CH | $R^2 = C_4H_9$         | 172.1° C. |
| 16 | N  | $R^2 = CH_2CH(CH_3)_2$ | 173.7° C. |
| 17 | CH | $R^2 = CH_2CH(CH_3)_2$ | 231.7° C. |
| 18 | N  | $R^1 = CH_2CF_3$       | 183.9° C.; $[\alpha]_D^{20} = -9.32°*$ (−)-(2S, cis) |
| 19 | N  | $R^1 = CH_2CF_3$       | 183.3° C.; $[\alpha]_D^{20} = +10.03°*$ (+)-(2R, cis) |
| 20 | N  | $R^2 = c.C_6H_{11}$    | 180.7° C. |
| 21 | CH | $R^2 = c.C_6H_{11}$    | 189.5° C. |
| 22 | CH | $R^1 = CH_2CF_3$       | 178.6° C. |
| 23 | N  | $R^1 = CHCH_3CF_3$     | 187.7° C. |
| 24 | N  | $R^2 = c.C_5H_9$       | 180.1° C. |
| 25 | CH | $R^2 = c.C_5H_9$       | 202.8° C. |
| 26 | N  | $R^2 = CH(CH_3)C(CH_3)_2$ | 154.0° C. |
| 27 | CH | $R^2 = CH(CH_3)C(CH_3)_2$ | 185.1° C. |

TABLE 2-continued

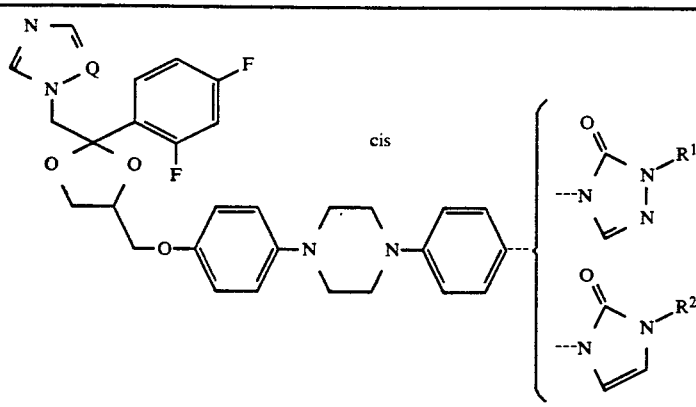

| Comp. No. | Q | $R^1$ or $R^2$ | Physical data |
|---|---|---|---|
| 28 | N | $R^1 = CH_2-CF_2-CHF_2$ | 184.5° C. |
| 29 | N | $R^2 = CH(C_2H_5)_2$ | 150.1° C. |
| 30 | CH | $R^2 = CH(C_2H_5)_2$ | 152.6° C. |
| 31 | N | $R^2 = CH(CH_3)\text{-}n\text{-}C_3H_7$ | 160.2° C. |
| 32 | CH | $R^2 = CH(CH_3)\text{-}n\text{-}C_3H_7$ | 141.9° C. |
| 33 | N | $R^1 = CH_2CH_2F$ | |
| 34 | N | $R^1 = CH(CH_3)CH_2F$ | |
| 35 | N | $R^1 = CH(CH_2F)_2$ | |
| 36 | N | $R^1 = CH(CH_3)C_2F_5$ | |

*: conc. = 1% in $CH_2Cl_2$

PHARMACOLOGICAL EXAMPLES

The antifungal activity of the compounds of formula (I) is clearly evidenced by the data obtained in the following experiments. Said data are supplemented to illustrate the useful antifungal properties of all the compounds (I) and not to limit the invention with respect to the scope of susceptible microorganisms nor with respect to the scope of formula (I).

EXAMPLE 12 a) Topical and oral treatment of vaginal candidosis in rats.

Female Wistar rats of ±100 g body weight were used. They were ovariectomized and hysterectomized and after three weeks of recovery, 100 mg of oestradiol undecylate in sesame oil was given subcutaneously once a week for 3 consecutive weeks. The thus induced pseudo-oestrus was controlled by microscopic examination of vaginal smears. Food and water were left available ad libitum. The rats were infected intravaginally with $8.10^5$ cells of *Candida albicans*, grown on Sabouraud broth for 48 hours at 37° C. and diluted with saline. The date of infection varied from day +25 to day +32 after surgical intervention, depending on the appearance of signs of inducing pseudo-oestrus. The drugs under investigation were administered topically in 0.2 ml PEG 200 twice a day or orally in PEG 200 once a day for three consecutive days starting from the third day after infection. For each experiment there were placebo treated controls. The results were assessed by taking vaginal smears with sterile swabs on several days after the infection. The swabs were put into Sabouraud broth in petri-dishes and incubated for 48 hours at 37° C. When the animals were negative at the end of the experiment, i.e., if no growth of *Candida albicans* occurred, this had to be due to drug administration because placebotreated controls were always positive. Table 3 shows the lowest effective oral dose (LED) (mg/kg bodyweight) and the lowest effective topical concentration (LEC) (%) of the drugs under investigation which were found to be active up to 7 days after the last topical administration of the drug.

TABLE 3

| | Vaginal Candidosis | |
|---|---|---|
| Co.Nr. | LED (mg/kg) oral | LEC (%) topical |
| 1 | 2.5 | 0.063 |
| 2 | 0.63 | 0.016 |
| 3 | 2.5 | 0.125 |
| 5 | 2.5 | ≦0.125 |
| 6 | 2.5 | ≦0.031 |
| 8 | 2.5 | 0.125 |
| 9 | 1.25 | <0.125 |
| 10 | 2.5 | 0.125 |
| 12 | 1.25 | ≦0.125 |
| 14 | 1.25 | <0.125 |
| 16 | 2.5 | <0.125 | b) Topical and oral treatment of microsporosis in guinea pigs.

Adult Albino guinea pigs were prepared by clipping their backs and infected on the scarified skin by scratching five 3 cm long transverse cuts with *Microsporum canis* (strain RV 14314). The animals were housed individually in wire mesh cages and food and water were available ad libitum. The drugs under investigation were administered topically once a day for 14 consecutive days starting the third day after infection. The oral treatment began on the day of infection and was continued once a day for 14 consecutive days. For each experiment there were placebo treated controls. The animals were evaluated 21 days after infection by microscopic examination of the skin and by cultures on Sabouraud agar comprising a suitable bacterial antibiotic and a suitable agent to eliminate contaminating fungi.

Table 4 contains the lowest effective oral dose (LED) (mg/kg bodyweight) and lowest effective topical concentration (LEC) (%) of the drugs under investigation at which no lesions were observed and at which there was no culture growth.

TABLE 4

| | Microsporum Canis | |
|---|---|---|
| Co.Nr. | LED (mg/kg) oral | LEC (%) topical |
| 1 | 1.25 | 0.063 |
| 2 | 1.25 | 0.063 |
| 3 | 1.25 | 0.063 |

COMPOSITION EXAMPLES

EXAMPLE 13: ORAL DROPS 500 grams of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 14: ORAL SOLUTION 9 grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining gram of the former solution and 12 l 1,2,3-propanetriol and 3 l of sorbitol 70% solution were added thereto. 40 grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 15: CAPSULES 20 grams of the A.I., 6 grams sodium lauryl sulfate, 56 parts starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE 16: FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 ml of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10.000 tablets, each containing 10 mg of the active ingredient.

Coating

To a solution of 10 grams methyl cellulose (Methocel 60 HG ®) in 75 ml of denatured ethanol there was added a solution of 5 grams of ethyl cellulose (Ethocel 22 cps ®) in 150 ml of dichloromethane. Then there were added 75 ml of dichloromethane and 2.5 ml 1,2,3-propanetriol. 10 grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension (Opaspray K-1-2109 ®) and the whole was homogenated. The tablet cores were coated with the thus obtained mixture in a coating apparatus.

EXAMPLE 17: INJECTABLE SOLUTION 1.8 grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

EXAMPLE 18: SUPPOSITORIES 3 grams A.I. was dissolved in a solution of 3 grams 2,3-dihydroxybutanedioic acid in 25 ml polyethylene glycol 400. 12 grams surfactant (SPAN ®) and triglycerides (Witepsol 555 ®) q.s. ad 300 grams were molten together. The latter mixture was mixed well with the former solution. The thus obtained mixture was poured into moulds at a temperature of 37°-38° C. to form 100 suppositories each containing 30 mg/ml of the A.I.

EXAMPLE 19: INJECTABLE SOLUTION 60 grams of A.I. and 12 grams of benzylalcohol were mixed well and sesame oil was added q.s. ad 1 l, giving a solution comprising 60 mg/ml of A.I. The solution was sterilized and filled in sterile containers.

EXAMPLE 20: 2% CREAM 75 mg Stearyl alcohol, 20 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70° to 75° C. while using a homogenizer for liquids. The resulting emulsion is allowed to cool to below 25° C. while continuously mixing. A solution of 20 mg of A.I. of formula (I), 1 mg polysorbate 80 and 637 mg purified water and a solution of 2 mg sodium sulfite anhydrous in purified water are next added to the emulsion while continuously mixing. The cream is homogenized and filled into suitable tubes.

We claim:

1. A compound having the formula

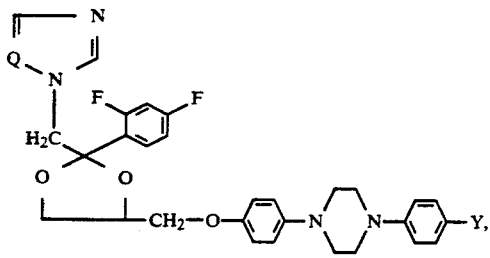

a pharmaceutically acceptable acid addition salt or a stereochemically isomeric form thereof, wherein
Q is CH or N;
Y is a radical of formula

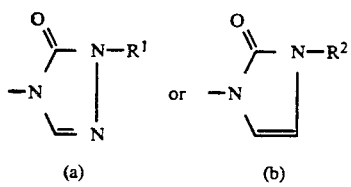

$R^1$ is $C_{5-7}$cycloalkyl or mono-, di-, tri-, tetra- or pentahalo$C_{1-4}$alkyl; and
$R^2$ is $C_{1-6}$alkyl, $C_{5-7}$cycloalkyl or mono-, di-, tri-, tetra- or pentahalo$C_{1-4}$alkyl.

2. A compound according to claim 1 wherein Q is N; and the substituents on the dioxolane nucleus have a cis configuration.

3. A compound according to claim 2 wherein $R^1$ and $R^2$ are mono-, di-, tri-, tetra- or pentafluoro$C_{1-4}$alkyl, cyclohexyl or cyclopentyl, or $R^2$ is $C_{1-4}$alkyl.

4. A compound according to claim 3 wherein $R^1$ and $R^2$ are 2,2,2-trifluoroethyl, 2,2,3,3-tetrafluoropropyl, cyclopentyl, or $R^2$ is propyl, 1-methylpropyl, 2-methylpropyl or butyl.

5. A compound according to claim 1 wherein the compound is
cis-2-cyclopentyl-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-3H-1,2,4-triazol-3-one;
cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(2,2,2-trifluoroethyl)-3H-1,2,4-triazol-3-one; or
cis-1-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-1,3-dihydro-3-(1-methylpropyl)-2H-imidazol-2-one.

6. An antifungal composition comprising an inert carrier and as active ingredient an antifungally effective amount of a compound as claimed in any of claims 1 to 5.

7. A method of inhibiting or preventing the growth or development of fungi, or of destroying fungi, in warm-blooded animals suffering from diseases caused by these fungi, by the systemic or topical administration to said warm-blooded animals of an antifungally effective amount of a compound as claimed in any of claims 1 to 5.

* * * * *